United States Patent
Bon et al.

(10) Patent No.: US 10,012,495 B2
(45) Date of Patent: Jul. 3, 2018

(54) OPTICAL TELEMETRY DEVICE

(71) Applicants: CENTRE NATIONAL DE LA RECHERCHE SCIENTIFIQUE-CNRS, Paris (FR); Université Paris-Sud, Orsay (FR)

(72) Inventors: Pierre Bon, Palaiseau (FR); Emmanuel Fort, Cachan (FR); Sandrine Leveque-Fort, Cachan (FR)

(73) Assignees: CENTRE NATIONAL DE LA RECHERCHE SCIENTIFIQUE—CNRS, Paris (FR); Université Paris-Sud, Orsay (FR)

( * ) Notice: Subject to any disclaimer, the term of this patent is extended or adjusted under 35 U.S.C. 154(b) by 0 days.

(21) Appl. No.: 15/516,254

(22) PCT Filed: Sep. 8, 2015

(86) PCT No.: PCT/EP2015/070503
§ 371 (c)(1),
(2) Date: Mar. 31, 2017

(87) PCT Pub. No.: WO2016/050460
PCT Pub. Date: Apr. 7, 2016

(65) Prior Publication Data
US 2017/0299375 A1    Oct. 19, 2017

(30) Foreign Application Priority Data
Oct. 3, 2014   (FR) ...................................... 14 59500

(51) Int. Cl.
G01B 11/14    (2006.01)
G01N 15/14    (2006.01)
(Continued)

(52) U.S. Cl.
CPC ................ *G01B 11/14* (2013.01); *G01B 9/04* (2013.01); *G01N 15/1463* (2013.01);
(Continued)

(58) Field of Classification Search
CPC .......................... G01B 11/14; G01B 2290/30
See application file for complete search history.

(56) References Cited

U.S. PATENT DOCUMENTS

| 6,031,611 A | 2/2000 | Rosakis et al. | |
| 2010/0141959 A1* | 6/2010 | Kuchel | G01J 9/0215 356/521 |
| 2013/0335746 A1* | 12/2013 | Huber | G01B 11/026 356/498 |

OTHER PUBLICATIONS

International Search Report issued in PCT/EP2015/070503 dated Dec. 8, 2015 (6 pages).
(Continued)

Primary Examiner — Jonathan Hansen
(74) Attorney, Agent, or Firm — Osha Liang LLP

(57) ABSTRACT

According to one aspect, the invention relates to a device (100, 200, 300, 400, 500) for measuring the distance, with respect to a reference plane ($P_{REF}$), from a point of light ($P_i$) of an object (O). The device comprises a two-dimensional detector (30) comprising a detection plane ($P_{DET}$) and an imaging system (10) adapted to form an image of a light spot ($P_i$) situated on an object of interest plane (11) in an image plane (11') arranged in the vicinity of the detection plane ($P_{DET}$) or a conjugate plane ($P'_{DET}$) of the detection plane. The device further comprises a separator element (20) for forming, from a beam emitted by a point of light of the object of interest plane (11), and emerging from the imaging system (10) at least two coherent beams, having a spatial superposition region in which the beams interfere and a signal processing means (50) for determining, from the interference pattern formed on the detection plane, and
(Continued)

resulting from the optical interferences between said coherent beams, the distance from the point of light to a conjugate plane of the detection plane in the object space of the imaging system (10), said conjugate plane of the detection plane forming the reference plane ($P_{REF}$).

10 Claims, 10 Drawing Sheets

(51) Int. Cl.
    *G01B 9/04*     (2006.01)
    *G02B 21/00*     (2006.01)
    *G01N 15/00*     (2006.01)
    *G01N 15/10*     (2006.01)

(52) U.S. Cl.
    CPC ....... *G02B 21/008* (2013.01); *G02B 21/0056* (2013.01); *G02B 21/0076* (2013.01); *G01B 2290/30* (2013.01); *G01N 2015/0065* (2013.01); *G01N 2015/1006* (2013.01)

(56) References Cited

OTHER PUBLICATIONS

Written Opinion of the International Searching Authority issued in PCT/EP2015/070503 dated Dec. 8, 2015 (6 pages).
Ruan Y et al., "Tomographic diffractive microscopy with a wavefront sensor", Optics Letters, Optical Society of America, US, vol. 37, No. 10, pp. 1631-1633, May 15, 2012 (3 pages).
Popescu G et al., "Diffraction phase microscopy for quantifying cell structure and dynamics", Optics Letters, Optical Society of America, US, vol. 31, No. 6, pp. 775-777, Mar. 15, 2006 (3 pages).
Amardeep S.G., et al., "Lateral shearing digital holographic imaging of small biological specimens", Optics Express, vol. 20, No. 21, p. 23617, Oct. 8, 2012 (6 pages).
B. Hajj et al., "Accessing the third dimension in localization-based super-resolution microscopy", Phys. Chem. Chem. Phys., 2014, 16, 16340-16348 (9 pages).
A. Backer et al., "A bisected pupil for studying single-molecule orientational dynamics and its applications to three-dimensional super-resolution microscopy", Applied Physics Letters 104, 193701 (2014) (5 pages).
S. Abrahamsson et al., "Fast multicolor 3D imaging using aberration-corrected multifocus microscopy", Nature Methods, vol. 10 No. 1 (2013) (6 pages).
G. Shtengel et al., "Interferometric fluorescent super-resolution microscopy resolves 3D cellular ultrastructure" Proc Natl Acad Sci USA 106, 3125 (2009) (6 pages).
J. Primot et al., Extended Hartmann test based on the pseudoguiding property of a Hartmann mask completed by a phase chessboard, Applied Optics, vol. 39, Issue 31, pp. 5715-5720 (2000) (6 pages).

\* cited by examiner

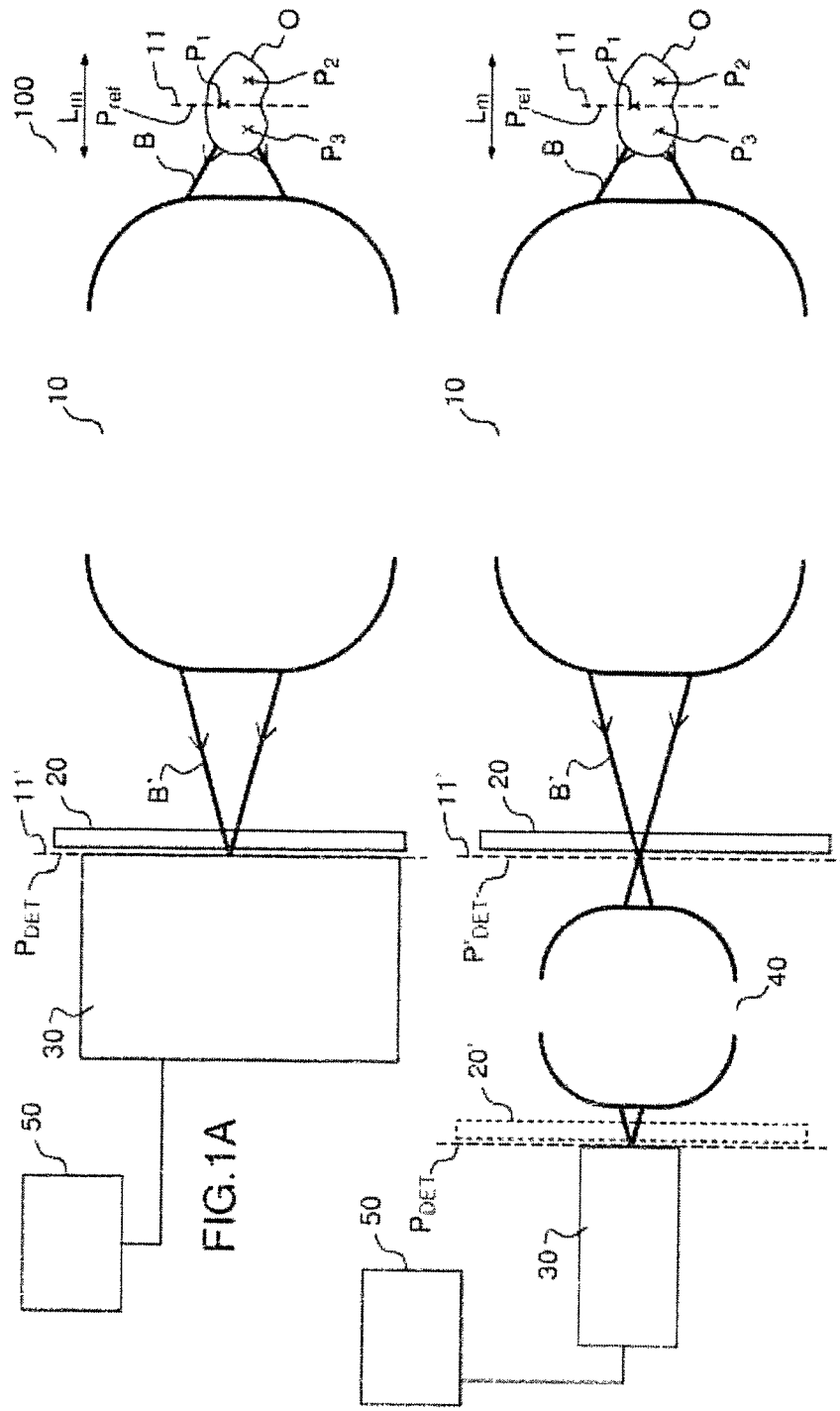

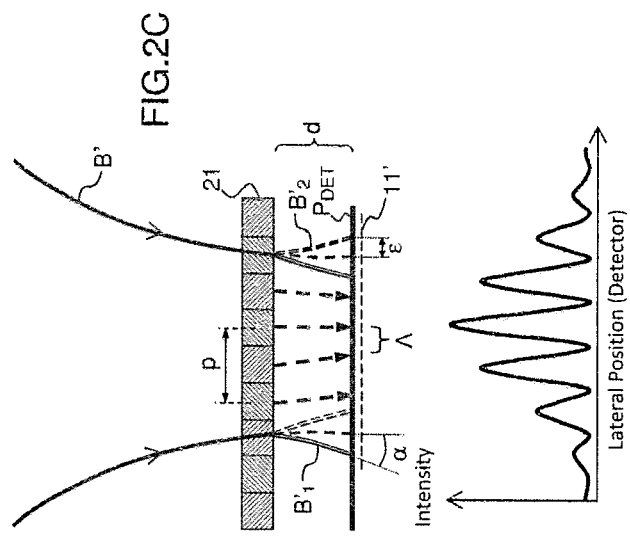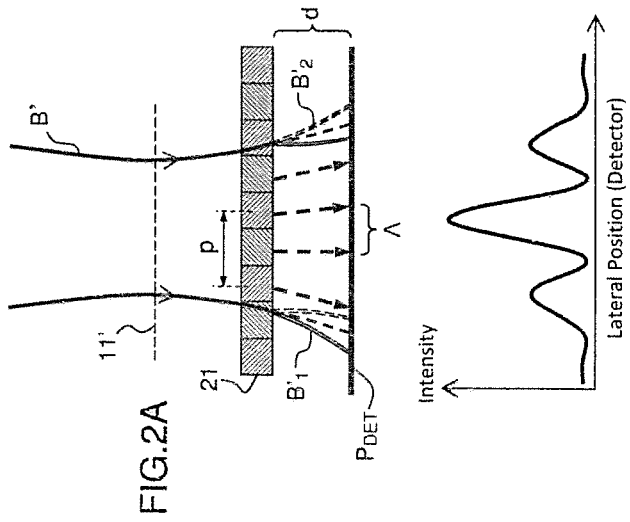

OPTICAL TELEMETRY DEVICE

STATE OF THE ART

Technical Field of the Invention

This invention relates to a method and an optical telemetry device to determine the three-dimensional position of an object and which applies in particular to three-dimensional microscopic imaging for biological objects, but also to passive optical telemetry (without time-of-flight measurement).

State of the Art

A few years after their introduction, the so-called super-resolution microscopy techniques have grown considerably in the field of biological specimen studies, in particular for studying the structure and spatial dynamics of protein assemblages (molecular complexes measuring between a few nanometers to a hundred nanometers) within the cell. At present, it is possible to functionalize virtually any protein in an organism by adding a fluorescent label thereto, which can be directly synthesized by the cell, or constituted by a fluorescent compound added within the sample. This results in the formation of emitters capable of emitting a number of photons comprised between a few hundred thousand and a few million before being photo-destroyed. Super-resolution techniques, known as the acronyms PALM for "Photo-Activated Location Microscopy" or (d)STORM for "(direct) Stochastical Optical Reconstruction Microscopy" for example, combining nanoscale localization and control of the number of simultaneously active transmitters, in order to obtain two-dimensional images of cell samples with a resolution of 10-50 nm, which is well below the conventional limit of diffraction.

However, these techniques are currently used principally for two-dimensional imaging; access to 3D organization of cellular structures at the nanoscale continues to present many difficulties. The review article by B. Hajj et al. ("Accessing the third dimension in localization-based super-resolution microscopy", Phys. Chem. Chem. Phys., 2014, 16, 16340-16348) presents a synthesis of the techniques used by three-dimensional super-resolution microscopy and combines these techniques into several categories: the techniques based on PSF shape control (acronym of "Point Spread Function" and representing the impulse response function of the imaging system), those based on a so-called "multi-plan" approach and techniques using interferometry.

Techniques based on shape control of the impulse response (PSF) of the imaging system comprising the microscope objective comprising the microscope objective to break the axial symmetry of the PSF so that there is a bijective relationship between the lateral section of the PSF and the axial position of the emitter with respect to the focal plane of the imaging system. A particular phase mask has recently been described (see A Backer et al., "A bisected pupil for studying single-molecule orientational dynamics and its application to three-dimensional super-resolution microscopy", Applied Physics Letters 104, 193701 (2014)) arranged on a pupillary plane of the microscope objective and dividing the lateral section of the PSF into two lobes, the relative position of the two lobes making it possible to determine the axial position of the emitter. However, in this technique as in other techniques of this type, it is not possible to simultaneously study a large density of molecules because as soon as the density of particles increases, lobe superposition is observed, or more in general, enlarged PSFs. Moreover, the optical aberrations naturally introduced by the sample in the case of deep imaging tend to eliminate the bijective relationship between the shape of the PSF and the axial position, which limits the use of these techniques in the first layers of cells.

The multi-plane approach consists in simultaneously imaging the signal of a transmitter in axially separate planes. The article by S. Abrahamsson et al. ("fast multicolor 3D imaging using aberration-corrected multifocus microscopy", Nature Methods, Vol. 10 No. 1 (2013)) thus describes, for example, the arrangement of a particular grating making it possible to generate nine images on a single detector corresponding to nine diffraction orders. However, a limitation of the multi-plane techniques is the division of the "photon budget" of the transmitter according to a given number of images, resulting in loss of sensitivity and therefore of precision.

Axial precision in super-resolution microscopy can be significantly improved by interfering waves emitted from the emitter at the focus of two microscope objectives (see G. Shtengel et al., "Interferometric fluorescent super-resolution microscopy resolves 3D cellular ultrastructure" Proc Natl Acad Sci USA 106, 3125 (2009)). This latter technique, which uses a so-called "4pi" measuring system, that is to say using two head-to-head objectives in order to collect light in almost 4 pi steradian, combined with a triple interferometric detection of the photons emitted, is that which today offers the best accuracy of axial localization, but at the cost of considerable experimental complexity which relegates it to a very minor use in biological laboratories. This technique is also sensitive to the differential aberrations resulting from the crossing of the sample forwards or backwards in a 4pi mounting, and this will work for any type of sample.

This invention implements an interferometric technique which does not have the disadvantages of the previously described techniques; in particular it enables full-field imaging suitable for detecting fluorescent emitter continuums, but requiring only a single detector. It is applicable in super-resolution microscopy but also in classical microscopy and also finds applications in passive optical telemetry, i.e., to determine the distance of an object in a scene without time-of-flight analysis.

SUMMARY OF THE INVENTION

According to a first aspect, the invention relates to a device for measuring the distance, with respect to a reference plane, of a point of light of an object, comprising:
- a two-dimensional detector comprising a detection plane;
- an imaging system adapted to form an image from a point of light located on an object-of-interest plane in an image plane situated close to the detection plane or a conjugate plane of the detection plane;
- a separator element making it possible to form, from a beam emitted by a light point from the object-of-interest plane and emerging from the imaging system, at least two beams being coherent with each other, having a spatial superposition region in which the beams interfere;
- signal processing means making it possible to determine, from the interference pattern formed on the detection plane and resulting from the optical interferences between said coherent beams, the distance from the point of light to a conjugate plane of the detection plane in the space that is the object of the imaging system (10), said conjugate plane of the detection plane forming the reference plane.

For the purposes of this description, the notion of "point of light" of an object or "source point" also extends broadly to an elementary zone of an object in which all emission points are spatially coherent to each other and together form a single image point on the detector. Thus, in the case of the application to super-resolution microscopy, a source point may be a fluorescent emitter or "quantum dot" whose spatial dimensions are smaller than the diffraction spot of the imaging system. In other macroscopic applications, on the contrary, a point source may encompass a zone that is more extended and spatially coherent of an object and that foams a "image point" on the detection plane the dimensions of which are significantly greater than those of the impulse response (or PSF) of the imaging system.

The device thus described makes it possible in particular to reconstruct an object in 3D without the need to implement a means for controlled illumination of the object; thus, the described device makes it possible, for example, to reconstruct in 3D an object emitting its own light (in the case of a fluorescent emitter in microscopy) or an object re-emitting light without having any control over its illumination (as in a scene of everyday life).

The separator element as defined in the device according to this description makes it possible to print within the "image point"—that is to say the image of a point of light of the object formed on the detection plane—a modulation whose period depends on the relative curvature of the wave coming from the light point, ultimately resulting in a relative elevation mapping of the object. The separator element coupled to the detector thus behaves like a curvature sensor of the wave coming from the different point of lights of the object which prints a modulation within each image point without degrading its resolution.

Advantageously, the separator element makes it possible to print a modulation within the image point whose period is small enough to form at least two fringes at the image point and to obtain sufficient accuracy in the measurement.

Advantageously, and in particular in the case of super-resolution microscopy applications, the period of the fringes of the interference pattern formed on the detection plane ("interfringe") is smaller than the diameter of the impulse response of the imaging system (or PSF), which is the smallest image formed from a point of light on the detection plane.

According to an embodiment, the separator element comprises a diffraction grating close to the imaging plane, for example a two-dimensional diffraction grating.

According to an embodiment, the diffraction grating is a transmission or reflection grating, which does not transmit, nor reflect, the zero-order.

According to an embodiment, the device is applied to three-dimensional imaging; the imaging system then includes a microscope objective.

According to an embodiment, the device also comprises a relay optic that makes it possible to form a conjugate plane of the detection plane in the image space of the imaging system.

According to a second aspect, the invention relates to a method for measuring the distance, with respect to a reference plane, of a point of light of an object of interest, comprising:

the formation of an image of the point of light in an image plane close to the detection plane of a two-dimensional detector or a conjugate plane of the detection plane;

the formation, by means of a separator element, from a beam emitted by the point of light and emerging from the imaging system of at least two beams that are coherent with each another and having a spatial superposition region in which the coherent beams interfere;

the determination, from the interference pattern formed on the detection plane and resulting from the optical interferences between said coherent beams, of the distance from the point of light to a conjugate plane of the detection plane in the space that is the object of the imaging system, said conjugate plane of the detection plane forming the reference plane.

According to an embodiment, the distance from the point of light to the reference plane is obtained from the measurement of the period of the fringes of the interference pattern.

BRIEF DESCRIPTION OF THE DRAWINGS

Other advantages and characteristics of the invention will become apparent upon reading the description, illustrated by the following figures:

FIGS. 1A and 1B, diagrams illustrating two examples of a telemetry device according to this description;

FIGS. 2A to 2D, diagrams illustrating the principle of the method implemented according to an example;

For the sake of consistency, identical elements are identified by the same references in the different figures.

DETAILED DESCRIPTION

Figure 3:
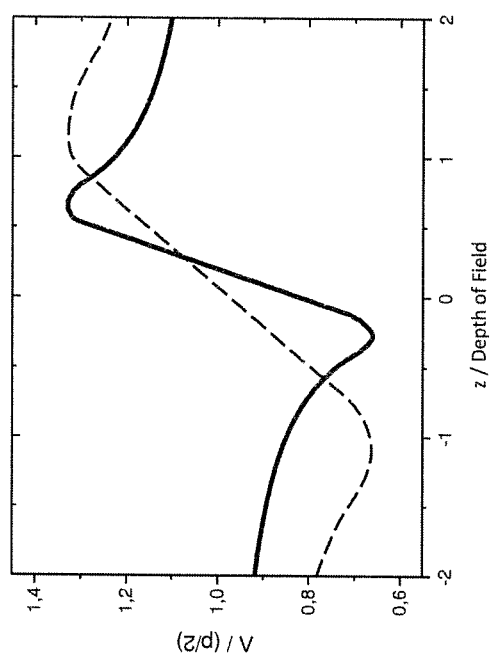
FIG. 3, curves showing, according to two particular examples, the value of the interfringe (pseudo-period of the modulation) as a function of the axial position of the source point with respect to the reference plane.

FIGS. 1A and 1B illustrate two examples of a telemetry device according to this description, adapted for measuring the distance, with respect to a given reference plane, from a point of light $P_i$ (or "source point") of an object of interest O in a scene.

The telemetry device 100 shown in FIG. 1A generally comprises a two-dimensional detector 30 with a detection plane $P_{DET}$ connected to a signal processing means 50 and an imaging system 10 adapted to form an image of a point of light $P_i$ of an object-of-interest plane 11, in an image plane 11' located near the detection plane 31 of the detector. In the telemetry device 200 shown schematically in FIG. 1B, the image plane 11' is located near a conjugated P'$_{DET}$ plane of the detection plane P$_{DET}$. The device further comprises a relay optic 40 making it possible to form a conjugate plane from the detection plane in the image space of the imaging system 10.

The proximity of the image plane to the detection plane (or the conjugate of the detection plane) depends on the accuracy of the distance measurement sought.

Indeed, for a given position of the detection plane P$_{DET}$ (or of the conjugate plane P'$_{DET}$ of the detection plane by the relay optics 40), it is possible to define, in the object space of the imaging system 10, a measurement zone defined on either side of an object plane P$_{REF}$ called "reference plane" and corresponding to the conjugate plane of the detection plane in the object space of the imaging system. The measurement zone corresponds to the zone in which the accuracy of the measurement of the distance from a point of light with respect to the reference plane is satisfactory as part of the envisaged application.

Thus, for example, in three-dimensional microscopic applications, when one is seeking an accurate location of an emitter with respect to the reference plane that is well below the subject-matter's depth of field in the imaging system, the measurement zone may have a total length L$_m$ that is less than four times the depth of field dz of the object in the imaging system and advantageously less than twice the depth of field dz of the object in the imaging system to ensure good measurement accuracy.

For a digital aperture imaging system NA, the depth of field of the object dz may be determined by $$dz = \frac{\lambda \cdot n}{NA^2} \quad (1)$$

With λ the average wavelength of the light collected and n the immersion index of the imaging system, i.e., the index of the medium situated just before the first dioptre (in the direction of light propagation) of the imaging system 10; typically n=1 for an immersion imaging system in air, for example for passive telemetry applications and n≈1.5 for an imaging system immersed in an immersion oil, for example, for super-resolution microscopy applications.

Consequently, in the case of, for example, applications in three-dimensional microscopy, the detection plane (or the conjugate of the detection plane) and the conjugate image plane 11' of the object-of-interest plane 11 by the imaging system 10 may be located at a distance from each other of less than twice the depth of field of the image in the imaging system, and advantageously at a distance of less than one time the depth of field of the image in the imaging system, so as to benefit from good accuracy in the measurement of the distance of the point of light.

In other applications, for example in passive telemetry applications, the distance between the detection plane (or the conjugate of the detection plane) and the conjugate image plane 11' of the object-of-interest plane 11 by the imaging system 10 can be extended to ten times, or even twenty times, the depth of field of the image, to the detriment of the location accuracy which consequently becomes on the order of the depth of field; this mode of operation is of interest mainly for measuring passive telemetry, where knowing where the object is located axially without super-resolution is sufficient.

Thus, in the example of FIGS. 1A and 1B, it is possible to measure not only the distance of point of light P$_1$, situated on an object-of-interest plane 11 substantially coincident with the reference plane P$_{REF}$, but also the distance between point of lights P$_2$ and P$_3$ located on either side of this reference plane, provided that they are located in the length measurement zone L$_m$ defined as a function of the accuracy sought.

To determine the distance from a point of light P$_i$ to the reference plane P$_{REF}$, the telemetry device comprises a separator element 20 making it possible to form, from a beam B' emitted by the point of light P$_i$ and emerging from the lighting system 10, at least two coherent beams (not shown in FIGS. 1A and 1B) and having a spatial superposition region in which said coherent beams interact with one another.

The separator element 20 will be described in greater detail hereinafter and may comprise, for example, a grating, advantageously a two-dimensional grating, located close to the detection plane P$_{DET}$ (example in FIG. 1A) or to the conjugated P'$_{DET}$ plane of the detection plane P$_{DET}$ (example in FIG. 1B). The separator element 20 may also comprise a separator slide or a separator cube, as will be illustrated by way of examples in the remainder of the description.

The separator element is arranged in such a way that the detection plane or the conjugate plane of the detection plane lies in the region of spatial superposition of the coherent beams with each other and coming from the separator element. Thus, on the detection plane of the detector, an image is formed for each source point P$_i$, which is the convolution of the impulse response of the imaging system (PSF) with an interference pattern resulting from the interference of the beams coming from the separator element.

By selecting the parameters of the separator element (for example the pitch of the grating in the case of a diffraction grating separator element, or the optical index and the thickness of the splitter slide in the case of a splitter slide type separator element), it is possible to set the interfringe of the interference figure and to print within the image a modulation whose period is advantageously smaller than the diameter Φ of the impulse response of the imaging system, given by:

$$\phi = 2r = 0.61 \frac{\lambda \cdot gy}{NA} \quad (2)$$

where r is the radius of the PSF, NA is the digital aperture of the imaging system and its magnification. As will be explained in detail hereinafter, the modulation period (in other words the interfringe of the interference pattern) depends on the relative position of the source point with respect to the reference plane P$_{REF}$ which is the conjugate plane of the detection plane P$_{DET}$ in the object space of the imaging system 10. The separator element thus described associated with the detector thus acts as a sensor of the relative curvature of the wave emitted by each source point of the object, to determine in fine the relative elevation mapping of the object.

FIGS. 2A to 2D illustrate in greater detail the principle of the method implemented according to a particular example in which the separator element comprises a grating 21.

The grating 21 is advantageously a two-dimensional diffraction grating. Two axial positioning measurements (e.g., distance measurements with respect to the reference plane) that are independent (one along each of the axes of the grating) can thus be obtained for a single source point, which increases the axial localization accuracy while making it possible to measure on images that may have any source distribution (continuum of fluorophores, scenes from everyday life . . . ).

The grating 21 is a transmission grating in accordance with an embodiment adapted to transmit all the incident light energy, i.e., a phase grating, when the assembly is in transmission, or it may be in accordance with a reflection grating variant adapted to reflect all the incident light energy when the assembly is in reflection. One or the other of these variants maximizes the signal-to-noise ratio of the 3D location.

Advantageously, a transmission or reflection grating must be chosen which barely transmit or reflect its zero-order of diffraction. This makes it possible to make the interferences formed by the diffracted orders independent of the light wavelength. Deleting the zero-order can be obtained, for example, by adjusting to $\pi$ [$2\pi$] the modulation of the phase shift introduced over a period, for example by etching the substrate of the grating or local modification of the index of the substrate. Another possibility for suppressing the zero-order is to suppress the zero-order in the Fourier space of the grating, but in this case, a loss of photons is introduced and therefore a loss of signal-to-noise ratio.

The pitch p of the grating is advantageously chosen so as to form more than one fringe per "image point" of a source point of the object, the image point being merged with the impulse response of the imaging system, or PSF, such as in super-resolution microscopy applications. Typically, the pitch of the grating comprised between one third of the radius of the image point and three times the radius of the image point may be chosen in order to have a lateral sampling of the fringes that is sufficient as well as limiting oversampling. Typically, a pitch p may be chosen on the order of the diameter of the image point, so as to have 2 fringes per image point; and in the case of a super-resolution microscopy application, a pitch p between r/3 and 3r, advantageously on the order of 2r, where r is the radius of the PSF given by the equation (2) above.

FIGS. 2A to 2D illustrate, by way of example and in a schematic manner, the propagation of the waves in the case of a measuring device comprising a diffraction grating 21 and the light intensity measured in a lateral direction in the plane of detection in the case of two source points positioned at two different axial positions.

To facilitate the theoretical demonstration, we assume in this example a one-dimensional grating of pitches p and it is assumed that the grating diffracts only the orders +1 and −1. For example, a complex amplitude grating as described for example in J. Primot et al. constitutes such a diffraction grating ("Extended Hartmann test based on the pseudoguiding property of a Hartmann mask completed by a phase chessboard", "Applied Optics, Vol. 39, Issue 31, pp. 5715-5720 (2000)). In practice, however, it is possible to prefer a grating that diffracts all orders except zero-order, such a grating being simpler to manufacture (phase grating with a "chessboard phase" pattern, for example, as described in the article quoted from Primot, et al.) and this makes it possible to prevent the loss of photons.

As can be seen in FIGS. 2B and 2D, a variation of the interfringe $\Lambda$ is observed as a function of the distance from the source point from the reference plane (i.e., the conjugate plane of the detection plane in the object space of the imaging system). The relationship between interfringe (period of modulation) and the distance of the source point considered from the reference plane can be determined theoretically from the parameters of the diffraction grating chosen, as is set out below in accordance with an example.

In the example shown in FIGS. 2A and 2C, the grating 21 is located at a distance d from the detection plane $P_{DET}$. In this example, the grating makes it possible to form two coherent diffracted beams denoted $B'_1$ and $B'_2$ and corresponding respectively to the +1 and −1 orders. The grating 21 diffracts the light on the order of +1 with an angle $\alpha$ with respect to the propagation of the direct light (i.e., zero-order of the grating, indicated by the simple dotted lines in the figures). In FIGS. 2A and 2C, the lateral offset between the point of impact on the detection plane of the diffracted order 1 and the (theoretical) point of impact of the zero-order is denoted by $\varepsilon$. The lateral offset corresponds to the half-lateral offset between the points of impact of the two "replicas" formed by the two coherent beams $B'_1$ and $B'_2$.

The wave vectors of the diffracted orders +1 and −1 corresponding to the beams $B'_1$ and $B'_2$ are respectively denoted:

$$k_{+1} = \frac{2\pi}{\lambda}\begin{bmatrix} \sin(\alpha) \\ \cos(\alpha) \end{bmatrix}_{(x,z)}$$

$$k_{-1} = \frac{2\pi}{\lambda}\begin{bmatrix} -\sin(\alpha) \\ \cos(\alpha) \end{bmatrix}_{(x,z)} \text{ with}$$

$$\sin(\alpha) = \frac{\lambda}{p}$$

where $\lambda$ is the wave length.

E denotes the scalar electromagnetic field coming from the image of the source point in the detection plane of the detector:

$$E(x) = A(x)e^{i\frac{2\pi}{\lambda}S(x)}$$

with A(x) as the amplitude of the field and with S(x) as the spherical wave surface related to the curvature of the wave front emitted from the source point by $(x) = x^2/2z$ with z as the distance of the image from the source point to the detection plane. The interferogram I (x) formed by the +1 and −1 orders on the detection plane located at the distance d from the grating can be described by:

$$I(x) = i_0(x)\left[1 + \cos\left(\frac{2\pi}{\lambda}[S(x-\varepsilon) - S(x+\varepsilon) + 2x \cdot \sin(\alpha)]\right)\right] \quad (3)$$

With $i_0(x) \approx A^2(x)$ $$\varepsilon = d \cdot \tan(\alpha) \approx d \cdot \frac{\lambda}{p} \quad (4)$$

By a Taylor expansion to the order 1 of equation (3) we deduce:

$$I(x) = i_0(x)\left[1 + \cos\left(\frac{4\pi}{p}\left[x - d\frac{\partial S}{\partial x}(x)\right]\right)\right] \text{ or} \quad (5)$$

$$I(x) = i_0(x)\left[1 + \cos\left(\frac{2\pi}{p/2\left[1 - \frac{d}{z}\right]}x\right)\right]$$

It is therefore concluded that the measured intensity signal has a carrier $i_0(x)$ (the PSF of the imaging system), modulated by a signal of period $$\Lambda = p / \left( 2 \left[ 1 - \frac{d}{z} \right] \right)$$

thus depending only on the distance z between the image of the source point and the detector (distance sought reported in the image space of the imaging system) and the distance d between the grating and the detection plane (fixed and known).

In the case illustrated above, as shown in equation (5), the choice of a grating in which the zero-order is suppressed makes it possible, in particular, to eliminate the dependence of the intensity signal with the wavelength and thus to free oneself from chromatic effects.

The approximation used to determine the equation (5) above gives a pitch of $\Lambda \to \pm\infty$ when $z \to d$. In a real case, a Gaussian beam approach may be considered; in this case $S \to 0$ (and therefore $\Lambda \to p/2$) when $z \to d$.

FIG. 3 illustrates the evolution of $\Lambda$ as a function of z with the Gaussian approach in the case of two lateral offset values $\varepsilon$, respectively $\varepsilon_1=10$ µm (full line curve) and $\varepsilon_2=4$ µm (curve outlined by a dotted line) with a diffraction grating of the type described by means of FIGS. 2A to 2D having a pitch=20 µm. The values $\varepsilon_1=10$ µm and $\varepsilon_2=4$ µm respectively correspond to values of the distance d between the grating and the detection plane $d_1=200$ µm and $d_2=80$ µm. On this curve, the interfringe $\Lambda$ measured is normalized by the half-period of the grating and the distance z is normalized as a function of the depth of field.

First of all, these two curves show that it is possible, beginning with the value of the interfringe, to determine the distance z between the image of a source point and the detector and therefore to deduce therefrom in the object space of the imaging system, the distance between a source point of the object and the reference plane. The curves in FIG. 3 also illustrate the shape of the curve as a function of the value of the lateral half-shift c between the replicas, the lateral half-shift being proportional to the distance d between the grating and the plane of detection. The curves show that by playing on s we can enlarge the zone along the optical axis where the measurement is possible but we lose the localization accuracy.

In all cases, the grating will advantageously be placed at a distance sufficiently close to the detection plane so that the lateral offset introduced between the replicas is smaller than the diameter of the image point, for example, the diameter of the PSF ($\phi$, equation (2)) in the case of its application in super-resolution microscopy. In other words, we will want to have:

$$\varepsilon \leq \phi \text{ or} \qquad (6)$$
$$d \leq 0.61 \cdot g_y \cdot \frac{p}{NA}$$

The inequality (6) is translated as a function of the choice of the microscope objective at a d/p ratio typically lower than a value between 10 and 50 depending on the choice of the microscope objective; thus for grating pitches typically between 10 and 30 µm, a distance d will be chosen to that is less than a value that can vary between ten microns and 1 mm depending on the choice of the microscope objective.

Although described in the case of a one-dimensional grating having two diffraction orders, the principle illustrated by means of FIGS. 2A to 2D extends to other examples of diffraction gratings, and in particular a two-dimensional grating allowing two independent axial measurements (one following each grating axis) for each source point.

As illustrated by means of FIGS. 2A to 2D and 3, the axial positioning of the source points forming an object can thus be obtained by measuring the period or the local frequency of the interferogram formed on the detection plane.

Advantageously, the positioning of each source point is determined by comparing the measured value of the period/local frequency of the interferogram formed on the detection plane with a calibration curve of the period/frequency as a function of the axial positioning of the source point. The calibration curve can be obtained either theoretically (as the curve shown in FIG. 3 for example) or experimentally by measurements of frequencies obtained on images of source points whose axial positioning is known.

In practice, the measurement of the period/local frequency of the interferogram formed on the detector can be obtained in several ways.

The measurement can be done in the direct space (i.e., directly on the image) by local automatic adjusting (fitting) of the image by a function describing the interferogram (see equation (1) above, for example). This makes it possible to go back to the local period of the interferogram.

The measurement can also be done by a local Fourier transform to find the main peak in the Fourier space, i.e., the local frequency in the image area considered.

Alternatively, it is also possible to proceed by a wavelet transform (intermediate case of the two preceding ones).

Of course, a diffraction grating as described above can be replaced by any system making it possible to generate an equivalent phase and/or absorption function, such as, for example, a spatial light modulator (SLM) or a deformable mirror. With an SLM, however, the need to work in polarized light leads to a loss of photons that is detrimental in particular in microscopic applications. With a deformable mirror, the limit comes from the reduced number of actuators which translates into a period that is too large for the equivalent grating.

Other types of separator elements may be integrated in the device according to this description to form the curvature sensor thus described. It is sufficient for such a separator element to make it possible to separate the incident beam emitted by the point of light into at least two coherent beams having a spatial superposition region in which the beams interfere.

Figure 4A:
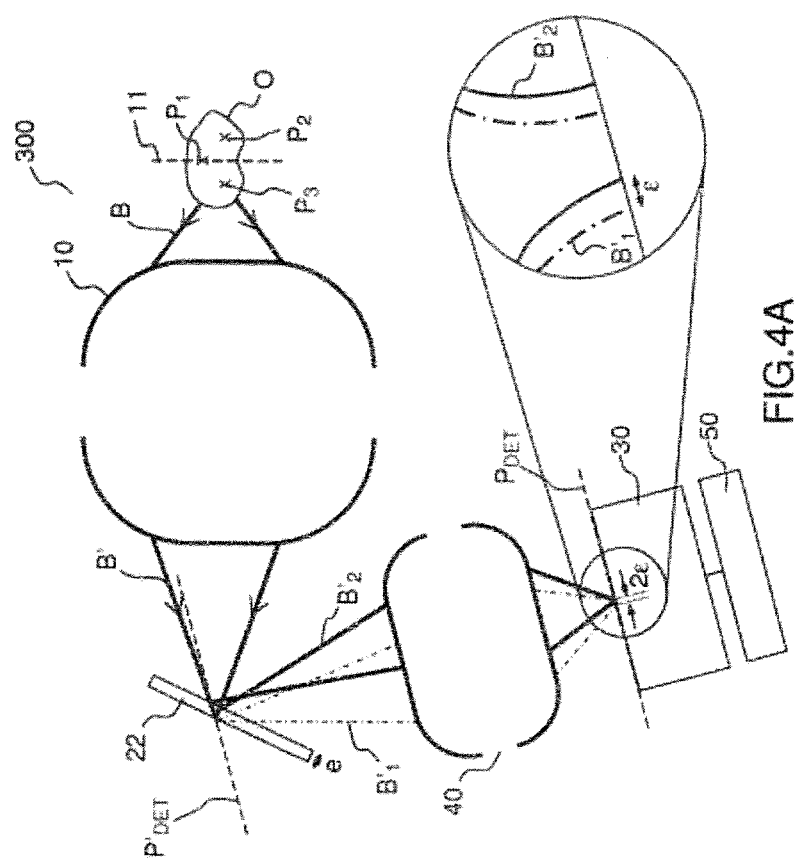
FIGS. 4A and 4B, diagrams illustrating telemetry devices according to two other examples.
Figure 4B:
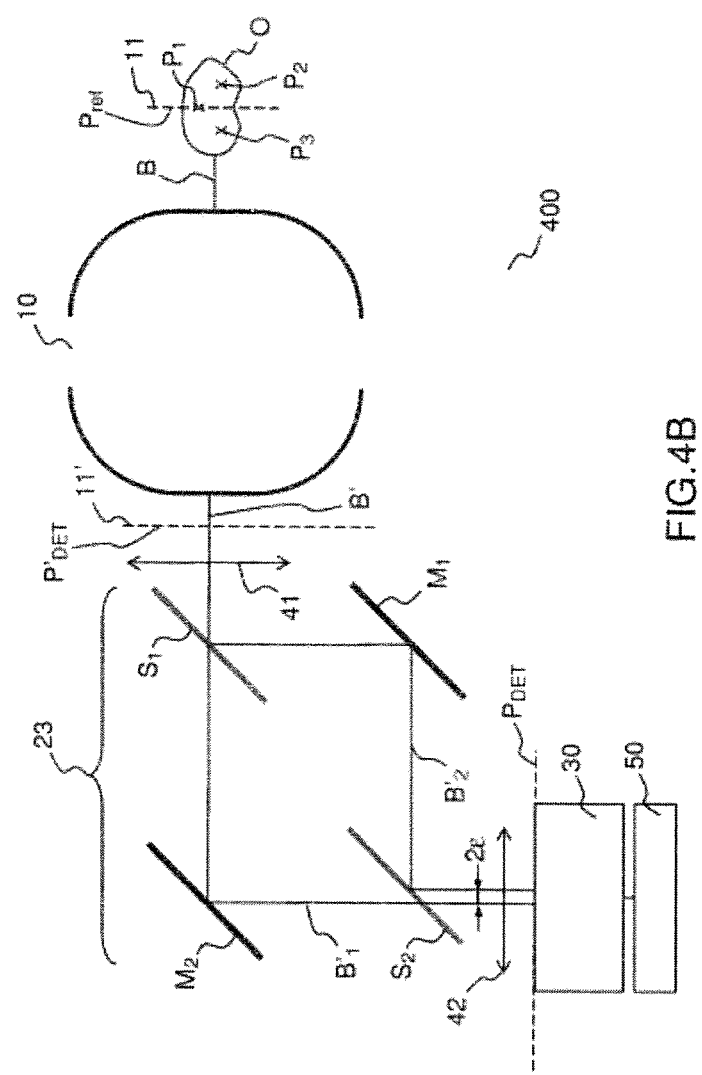

FIGS. 4A and 4B thus illustrate two examples of measuring devices according to this description. In the example of FIG. 4A, the separator element comprises a separating slide, for example a semi-reflecting slide, in order to form an interferometer assembly of the Murty interferometer type and in the example of FIG. 4B, the separator element comprises a separator cube to form a Mach-Zender type interferometer.

The telemetry device 300 shown in FIG. 4A comprises, as in the example of FIG. 1B, a two-dimensional detector 30 with a detection plane $P_{DET}$ and an imaging system 10 adapted to form an image of a source point $P_i$ of an object-of-interest plane 11 in an image plane 11' close to a conjugated $P'_{DET}$ plane of the detection plane $P_{DET}$, the device further comprising a relay optic 40 making it possible to conjugate the plane P'$_{DET}$ with the detection plane P$_{DET}$.

In the example of FIG. 4A, the telemetry device 300 further comprises a semi-reflecting slide 22 of thickness e, for example a glass slide of index n, arranged to allow partial reflection on each of the glass-air interfaces in such a way as to form two coherent beams, referenced B'$_1$ and B'$_2$ in FIG. 4A, which have a spatial superposition region in which the beams can interfere. In the example of FIG. 4A, the semi-reflecting slide is arranged in such a way as to form a 45° angle with the optical axis of the imaging system, to form an interferometer known as a Murty interferometer.

As in the theoretical description previously described on the basis of the use of a grating, the interferogram I(x) formed on the detection plane by the image of a source point at a distance z from the image by the relay imaging system (40) of the semi-reflecting slide (here coincident with the plane of the detector) may be described by:

$$I(x) \approx i_0(x)\left[1 + \cos\left(\frac{2\pi}{\lambda}[S(x-\varepsilon) - S(x+\varepsilon)]\right)\right] \quad (7)$$

$$I(x) \approx i_0(x)\left[1 + \cos\left(\frac{4\pi}{\lambda}\frac{\varepsilon}{z}x\right)\right]$$

(Gaussian Hypothesis)
However, in this example, the parameter ε is written:

$$\varepsilon = \frac{\sqrt{2}}{2} e \times \tan\left(\sin^{-1}\left(\frac{\sqrt{2}}{2n}\right)\right)$$

$$\varepsilon \approx \frac{\sqrt{2}}{4} e \text{ for } n = 1.6$$

With n as the index of the glass constituting the glass slide and e the thickness of the slide.

The telemetry device 400 shown in FIG. 4B comprises, as in the example of FIG. 1B, a two-dimensional detector 30 with a detection plane P$_{DET}$ and an imaging system 10 adapted to form an image of a source point P$_i$ of an object-of-interest plane 11 in an image plane 11' close to a conjugated P'$_{DET}$ plane of the detection plane P$_{DET}$, the device further comprising a relay optic making it possible to conjugate the plane P'$_{DET}$ with the detection plane P$_{DET}$.

In this example, the relay optic comprises two optics 41, 42, between which is arranged the separator element formed here by a Mach-Zender 2 interferometer. In this example, the interferometer comprises a separator plate S$_1$ (or a separator cube) making it possible to form two coherent beams B'$_1$ and B'$_2$, from the B' beam originating from source point P$_i$ and emerging from the imaging system 10. These beams propagate into two independent arms each containing a total reflection mirror (M$_1$, M$_2$). The beams are recombined by means of the separating cube (or slide) S$_2$. The beams are symbolized for the sake of clarity in FIG. 4B by their optical axis.

As in the previous example, an offset 2ε between the beams B'$_1$ and B'$_2$ is generated. The displacement can be obtained and adjusted either by displacing one of the separating plates (S$_1$, S$_2$) transversely to the optical axis or by tilting one of the mirrors (M$_1$, M$_2$). The same equation (7) results as in the case of the Murty interferometer.

Among the three examples of separator elements described, the diffraction grating makes it possible to obtain a greater measurement stability because the free-space propagation lengths of the coherent beams interfering with one another are smaller and also because of the fact that the number of free parameters influencing the measurement is smaller (in particular the angle of the separating slide in the case of the Murty interferometer and mirror angles and semi-reflective slides in the case of the Mach Zender interferometer). The diffraction grating also makes it possible to work with all the photons coming from the source point, which is not the case for the Mach Zender assembly, for example. It is therefore preferable to use the diffraction grating as a separator element. As explained above, the grating may also, in case of suppression of the zero-order, make it possible to form achromatic interferences, unlike the other separator elements.

Figure 5:
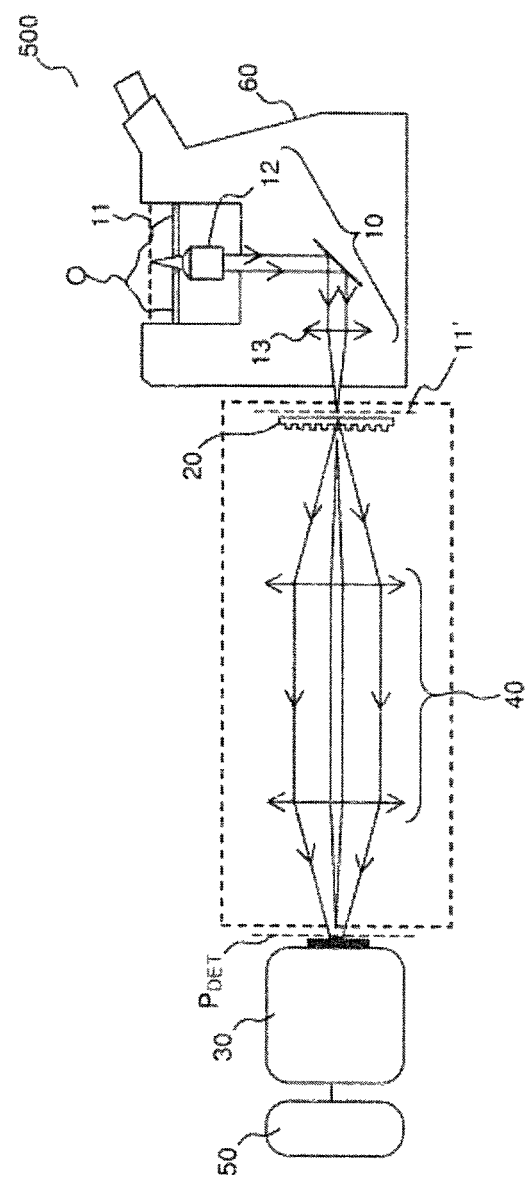
FIG. 5, a diagram illustrating an example of a device according to this description, applied to three-dimensional microscopic imaging.

FIG. 5 shows a diagram illustrating an example of a device according to this description, applied to three-dimensional microscopic imaging, in particular for imaging biological specimens formed from molecular complexes. Molecular complexes, whose average sizes are typically a few nanometers for small complexes to about 100 nanometers for the most imposing structures, are labeled according to known techniques by a probe capable of emitting a light signal, for example a fluorescent probe, thereby forming emitting particles having dimensions smaller than the diffraction limit of the optical system used to form an image thereof. The particles that are to be localized evolve in a embedding medium which may be liquid or solid, for example in the form of a gel, for example, a biological medium. The embedding medium may be arranged directly on a sample holder, deposited on a slide or held between two plates, for example glass plates. The embedding medium and the emitting particles, evolving therein and the holding plate(s), if any, are referred to as object O (FIG. 5).

The three-dimensional imaging device 500 comprises, in the example of FIG. 5, an imaging system 10 capable of forming an image on a detection plane P$_{DET}$ of a detector 30, advantageously, of the emitting particle (i.e., the source point) a matrix detector, for example a CCD, CMOS camera, an amplified camera of the EMCCD type (abbreviation of the English expression "Electron Multiplying Coupled Charge Display"), an sCMOS camera, a matrix of photomultipliers.

The imaging system 10 comprises, in this example, a microscope objective 12, corrected for example for an optical focal focus—infinite working configuration, associated with an objective lens 13 called a tube lens, making it possible to form an image on an intermediate detection plane 11'. The objective microscope and tube lens assembly forms a classical microscope optical system.

The imaging device 500 further comprises relay lenses 40 making it possible to form a conjugated P'$_{DET}$ plane of the detection plane P$_{DET}$ of the detector 30 in the image space of the imaging system 10, the image plane 11' being located in the vicinity of the conjugate P'$_{DET}$ plane. Due to the very small size of the emitting particles (less than the diffraction limit of the imaging system), the image, which is the convolution of the object with the impulse response of the imaging system or PSF, is here substantially coincident with the impulse response. A motorized platform (not shown) may be present and allows the sample O to be moved on an XY plane perpendicular to the optical axis of the microscope objective. A mechanical axial focusing device (not shown) may be present allowing the axial position of the sample to be adjusted with respect to the object focal plane of the microscope objective 12 and to image thusly the area of interest. The sample holder, the motorized platform, the axial focusing device, the microscope objective 12 and the tube lens 13 are arranged in a microscope body 60 of known type. The microscope body may also comprise, in the conventional manner, an eyepiece, a source for illuminating the sample associated with a condenser.

In the example of FIG. 5, the microscope body is of the inverted type (microscope objective positioned under the sample), but it might equally well be a right microscope (microscope objective above the sample).

The imaging device 500 also comprises a separator element 20, for example a two-dimensional grating close to the conjugate plane $P'_{DET}$ for the formation of at least two coherent beams having a region of spatial superposition at the detector, so as to implement the method of determining the distance according to this description.

As previously described, the grating is for example a phase grating making it possible to suppress the zero-order and whose pitch is chosen to form interferences of period less than the lateral resolution of the microscope on the detector. It is arranged perpendicularly to the optical axis in such a way that the coherent replicas between them are superimposed and can interfere with one another.

Figure 6A:
FIGS. 6A to 6C, images illustrating different pitches of the telemetry method in a super resolution microscope application implemented using a mounting of the type shown in FIG. 5 and with a biological sample comprising CHO cells ("Chinese Hamster Ovary") and a labeling of the tubulin proteins from the cytoskeleton of these cells.
Figure 6B:
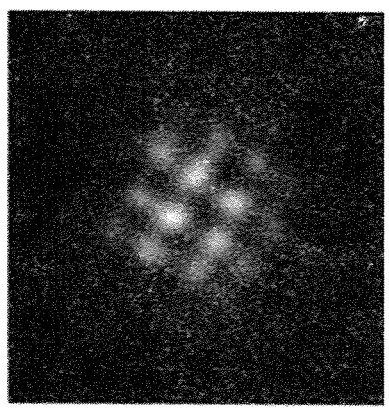
Figure 6C:
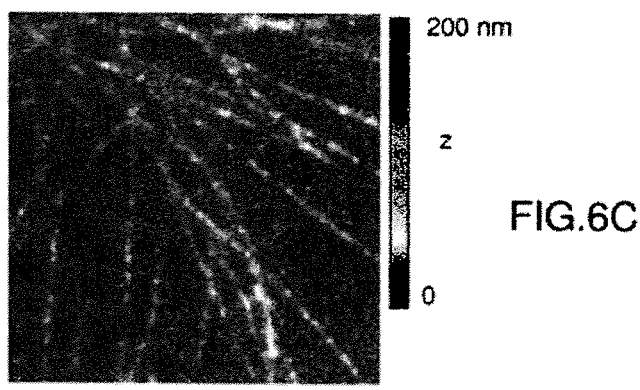

FIGS. 6A to 6C show images obtained at different stages of application of the method according to this description, in a super-resolution microscopy application implemented with a device of the type shown in FIG. 5.

Object O is a biological sample of CHO cells (Chinese Hamster Ovary) fixed with paraformaldehyde. The tubulin proteins of the cell cytoskeleton were labeled with fluorescent antibodies. The fluorescent probes are of the Alexa 647 type and the sample is observed by means of a CMOS-type matrix detector 30 using the dSTORM technique, in which blinking is achieved by using the Vectashield mounting product (Vectro Labs) and the use of a laser at 635 nm.

FIG. 6A shows a fluorescence image at the beginning of a dSTORM acquisition; the density of the fluorescent molecules is still important, resulting in a spatial continuum of fluorescence emission. However, interference can already be seen. FIG. 6B shows a zoom on a part of the image being acquired in which the emitter density is lower; we observe the response of a single fluorescent emitter (quantum dot) within which we distinguish the modulation resulting from the interference of the coherent replicas between them. The periodicity of this modulation makes it possible to determine the axial positioning of the emitter with respect to the reference plane, as explained above. The lateral positioning is obtained by determining the centroid of the spot (or image point) by barycenter or ideally by adjusting the spot with a Gaussian describing the PSF of the imaging system 10, after suppression of the modulation by filtering (low-pass frequency) of the spot. FIG. 6C shows the dSTORM reconstructed 3D image by 3D localization of each fluorescence emitter according to this description (as in 6B) thanks to the stochastic blinking of the emitters, the gray scale representing the axial positioning of the emitters These images illustrate the application of this method even on fluorescence continuums on which standard 3D imaging methods (e.g., techniques based on PSF shape control would not work).

Figure 7C:
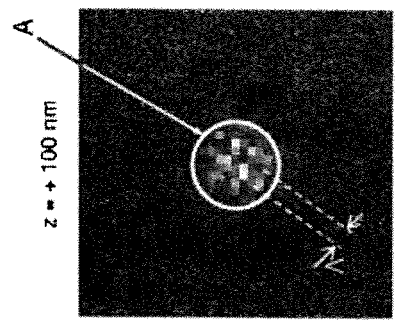
FIGS. 7A to 7C, images showing the shape of the interference pattern obtained for a single fluorescent emitter (quantum dot), at different axial positions, in a similar configuration (mounting and sample) to that used for the obtaining images 6A to 6C.
Figure 7B:
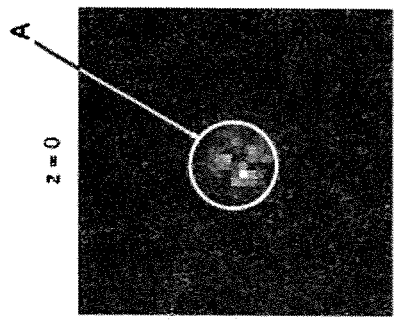
Figure 7A:
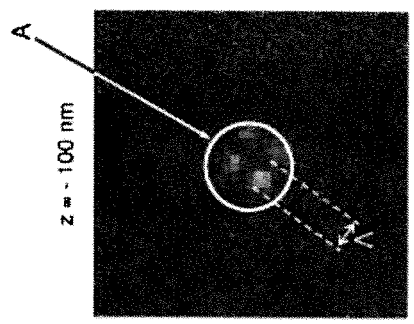

FIGS. 7A, 7B, 7C show experimental measurements of the light distribution measured using a 500 type mounting in the presence of single fluorescent emitters (of the nanocrystal semiconductor or quantum dot type) located either in a conjugate plane of the detector (7B) or before (7C), or after (7A) while remaining in the depth of field (i.e., no variation in the image size). It is clearly seen that the interfringe $\Lambda$ changes in function of the axial positioning of the emitter (i), and (ii) the size of the image of the transmitter is not enlarged compared to conventional imaging (circle of confusion).

Figure 8A:
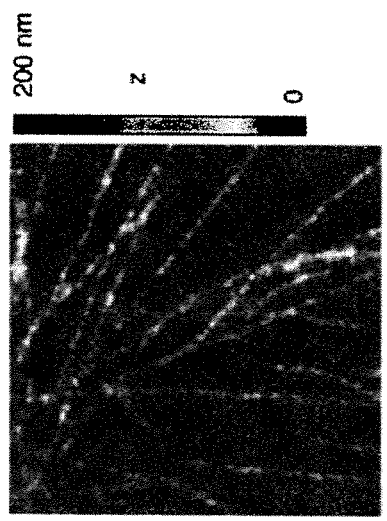
FIGS. 8A, 8B, respectively, a standard fluorescence image and an image of the biological sample obtained in a similar configuration (assembly and sample) with that used for obtaining images 6A to 6C.
Figure 8B:
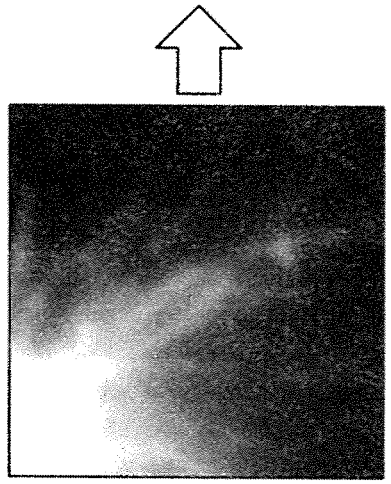

By way of comparison, FIGS. 8A and 8B represent experimental images of the same biological sample obtained by a standard epi-fluo (8A) imaging technique and dSTORM 3D imaging using the technique proposed in this description (8B) again on a CHO cell (Chinese Hamster Ovary) fixed with paraformaldehyde. The gain in lateral resolution (8B) with respect to 8A and the axial positioning allowing to follow the 3D spatial evolution of the cytoskeleton are clearly observed.

In addition to applications in three-dimensional microscopy, the applicants have shown that the method for measuring distance according to this description may also be applied to "passive" telemetry, that is to say without time-of-flight measurement, for measuring distances of objects in a scene.

Figure 9:
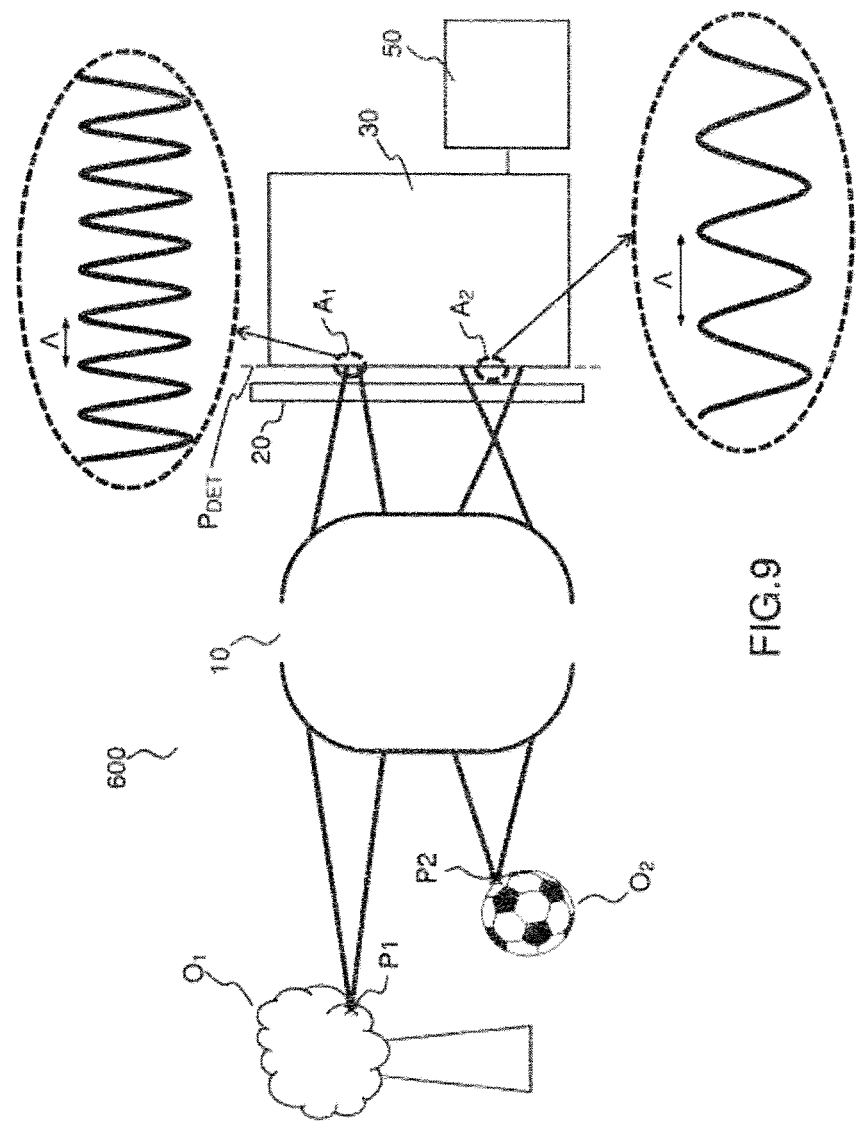
FIG. 9, a diagram of a device according to this description, applied to passive optical telemetry in a scene.

FIG. 9 thus shows a scene with several objects $O_1$, $O_2$, situated at different distances from a measuring device 600. The objects are illuminated in natural light and the natural light is backscattered so that each point of an object $O_i$ forms a source point $P_i$.

The device 600 comprises, as above, a detector 30 with a detection plane $P_{DET}$, an imaging system 10 adapted to form an image in an image plane from the scene in the vicinity of the detection plane $P_{DET}$, and a separator element 20, for example, a diffraction grating close to the detection plane $P_{DET}$, and which makes it possible to form at least two coherent beams ("replicas") having a region of spatial superposition in which the beams interfere. The imaging system 10 comprises, for example, a photo or video lens adapted to work at infinity.

Reconstruction of the axial positioning of the source points can be done in a volume of a few times the depth of field (~10×) of the imaging system. The axial resolutions are on the order of the depth of field and up to 1/100 of the latter. Depending on the photo or video lens used (aperture, focal length), the absolute values of the axial resolution and the depth of field change. It may be advantageous to adjust the aperture given a focal length so that the dynamic of the axial positioning measurement of the various points of the object encompasses all the objects of interest in a given scene; that is to say that the objects of interest are comprised in a few times the depth of field. Also, if the focal length and the aperture are fixed, the lateral offset modification e (for example, in the case of using a grating, translating along the optical axis with respect to the detection plane) allows adjustment of the axial positioning measurement dynamics with the described technique in order to obtain a reconstruction of all the objects of interest of the scene.

In this embodiment, the measurement of the variation of the interfringe from one point to another makes it possible to trace back to the 3D profile of the constituents of the scene.

Although described in a number of exemplary embodiments, the telemetry optical method according to the invention and the device for implementing said method comprise various variants, modifications and improvements which will be obvious to those skilled in the art, it being understood that these various variants, modifications and improvements form part of the scope of the invention as defined by the following Claims.

The invention claimed is:

1. A device for measuring the distance from a point of light of an object relative to a reference plane, comprising:
    a two-dimensional detector comprising a detection plane;
    an imaging system adapted to form an image from a point of light located on an object-of-interest plane in an image plane situated close to the detection plane or a conjugate plane of the detection plane;
    a separator element configured to form, from a beam emitted by a light point from the object-of-interest plane and emerging from the imaging system, at least two beams being coherent with each other, having a spatial superposition region in which the beams interfere; and
    signal processing means configured to determine, from the interference pattern formed on the detection plane and resulting from the optical interferences between said coherent beams, the distance from the point of light to a conjugate plane of the detection plane in the space that is the object of the imaging system, said conjugate plane of the detection plane forming the reference plane.

2. The device according to claim 1, wherein a period of the fringes of the interference pattern formed is smaller than the resolution of the imaging system.

3. The device according to claim 1, wherein the separator element comprises a diffraction grating close to the imaging plane.

4. The device according to claim 3, wherein the diffraction grating is a two-dimensional diffraction grating.

5. The device according to claim 3, wherein the diffraction grating is a transmission or reflection grating, which does not transmit, nor reflect, the zero-order.

6. The device according to claim 1, further comprising a relay optic configured to form a conjugate plane of the detection plane in the image space of the imaging system.

7. The device according to claim 1, applied to three-dimensional microscopic imaging, wherein the imaging system includes a microscope objective.

8. The device according to claim 1, applied to passive telemetry, wherein the imaging system includes a photo or video lens adapted to work to infinity.

9. A method for measuring a distance, with respect to a reference plane, from a point of light of an object of interest, comprising:
    the formation of an image from the point of light located on an image plane located near a detection plane of a two-dimensional detector or of a conjugate plane of the detection plane;
    the formation, by a separator element, from a beam emitted by the point of light and emerging from the imaging system, of at least two beams that are coherent with each another and having a spatial superposition region in which the coherent beams interfere; and
    the determination, from the interference pattern formed on the detection plane and resulting from the optical interferences between said coherent beams, of the distance from the point of light to a conjugate plane of the detection plane in the space that is the object of the imaging system, said conjugate plane of the detection plane forming the reference plane.

10. The method according to claim 9, in which the distance from the point of light to the reference plane is obtained from the measurement of a period of the fringes of the interference pattern.

* * * * *